(12) United States Patent
Kenny et al.

(10) Patent No.: US 12,268,826 B2
(45) Date of Patent: Apr. 8, 2025

(54) INTRODUCER SHEATH

(71) Applicant: HARMONY MEDICAL LIMITED, Dublin (IE)

(72) Inventors: Damien Kenny, Dublin (IE); Brian Bailey, Booterstown (IE); Kevin Walsh, Dublin (IE); John Hynes, Howth (IE)

(73) Assignee: Harmony Medical Limited, Dublin (IE)

( * ) Notice: Subject to any disclaimer, the term of this patent is extended or adjusted under 35 U.S.C. 154(b) by 1055 days.

(21) Appl. No.: 17/271,362

(22) PCT Filed: Sep. 3, 2019

(86) PCT No.: PCT/EP2019/073487
§ 371 (c)(1),
(2) Date: Feb. 25, 2021

(87) PCT Pub. No.: WO2020/049000
PCT Pub. Date: Mar. 12, 2020

(65) Prior Publication Data
US 2021/0196929 A1    Jul. 1, 2021

(30) Foreign Application Priority Data

Sep. 6, 2018 (EP) .................................. 18193070

(51) Int. Cl.
*A61F 2/24* (2006.01)
*A61B 17/00* (2006.01)
(Continued)

(52) U.S. Cl.
CPC ....... *A61M 25/0662* (2013.01); *A61F 2/2433* (2013.01); *A61F 2/2436* (2013.01);
(Continued)

(58) Field of Classification Search
None
See application file for complete search history.

(56) References Cited

U.S. PATENT DOCUMENTS 5,176,647 A * 1/1993 Knopfler ............ A61M 25/0113
604/181
5,368,574 A * 11/1994 Antonacci ......... A61M 39/0606
604/167.02
(Continued)

FOREIGN PATENT DOCUMENTS

| AU | 2003239407 B2 * | 10/2008 | ......... A61B 17/3417 |
| CA | 2447100 A1 * | 5/2002 | |
| JP | 2005525130 A * | 6/2002 | |

OTHER PUBLICATIONS

International Search Report issued in PCT/EP2019/073487; mailed Dec. 20, 2019.

*Primary Examiner* — Ann Hu
(74) *Attorney, Agent, or Firm* — Studebaker Brackett PLLC

(57) ABSTRACT

An introducer sheath for use in hybrid procedures on the heart includes a shaft having a distal balloon which is inflated inside the heart wall. A proximal collar is slidable along the shaft and locked to anchor the sheath to the wall of the heart. The sheath has markings visible to both the naked eye and under fluoroscopy to aid in judging the depth of insertion.

17 Claims, 17 Drawing Sheets

(51) Int. Cl.
*A61F 2/95* (2013.01)
*A61F 2/958* (2013.01)
*A61F 2/966* (2013.01)
*A61M 25/00* (2006.01)
*A61M 25/01* (2006.01)
*A61M 25/06* (2006.01)
*A61M 25/09* (2006.01)
*A61M 25/10* (2013.01)
*A61B 17/34* (2006.01)
*A61M 29/02* (2006.01)

(52) U.S. Cl.
CPC .............. *A61F 2/958* (2013.01); *A61F 2/966* (2013.01); *A61M 25/1002* (2013.01); *A61M 25/1025* (2013.01); *A61B 17/3468* (2013.01); *A61M 29/02* (2013.01)

(56) References Cited

U.S. PATENT DOCUMENTS

| | | | | |
|---|---|---|---|---|
| 5,868,755 | A * | 2/1999 | Kanner | A61F 2/958 606/198 |
| 6,190,393 | B1 * | 2/2001 | Bevier | A61F 2/958 623/1.11 |
| 7,691,089 | B2 * | 4/2010 | Gresham | A61B 17/3417 604/174 |
| 8,728,153 | B2 * | 5/2014 | Bishop | A61M 25/104 623/2.11 |
| 11,752,303 | B2 * | 9/2023 | Fischell | A61B 5/24 604/113 |
| 11,786,233 | B2 * | 10/2023 | Desjardin | A61B 17/3421 600/184 |
| 11,931,258 | B2 * | 3/2024 | Manash | A61F 2/2436 |
| 2002/0165489 | A1 * | 11/2002 | McGuckin, Jr. | A61M 25/0662 606/198 |
| 2004/0111061 | A1 * | 6/2004 | Curran | A61B 17/3421 604/174 |
| 2005/0251187 | A1 * | 11/2005 | Beane | A61B 17/32053 606/180 |
| 2006/0135962 | A1 * | 6/2006 | Kick | A61M 25/0662 606/191 |
| 2007/0078386 | A1 * | 4/2007 | Salazar | A61M 25/04 604/96.01 |
| 2007/0265643 | A1 * | 11/2007 | Beane | A61F 2/064 606/153 |
| 2008/0086166 | A1 * | 4/2008 | Ravikumar | A61B 17/3417 606/192 |
| 2008/0306442 | A1 * | 12/2008 | Bardsley | A61B 17/3439 604/164.04 |
| 2009/0287183 | A1 * | 11/2009 | Bishop | A61M 25/0662 604/509 |
| 2011/0112622 | A1 * | 5/2011 | Phan | A61F 2/95 623/1.11 |
| 2011/0144690 | A1 | 6/2011 | Bishop et al. | |
| 2011/0184337 | A1 * | 7/2011 | Evans | A61P 9/12 604/523 |
| 2012/0221092 | A1 * | 8/2012 | Jaffe | A61B 17/12136 604/533 |
| 2013/0053792 | A1 | 2/2013 | Fischell et al. | |
| 2015/0173782 | A1 | 6/2015 | Garrison et al. | |

* cited by examiner

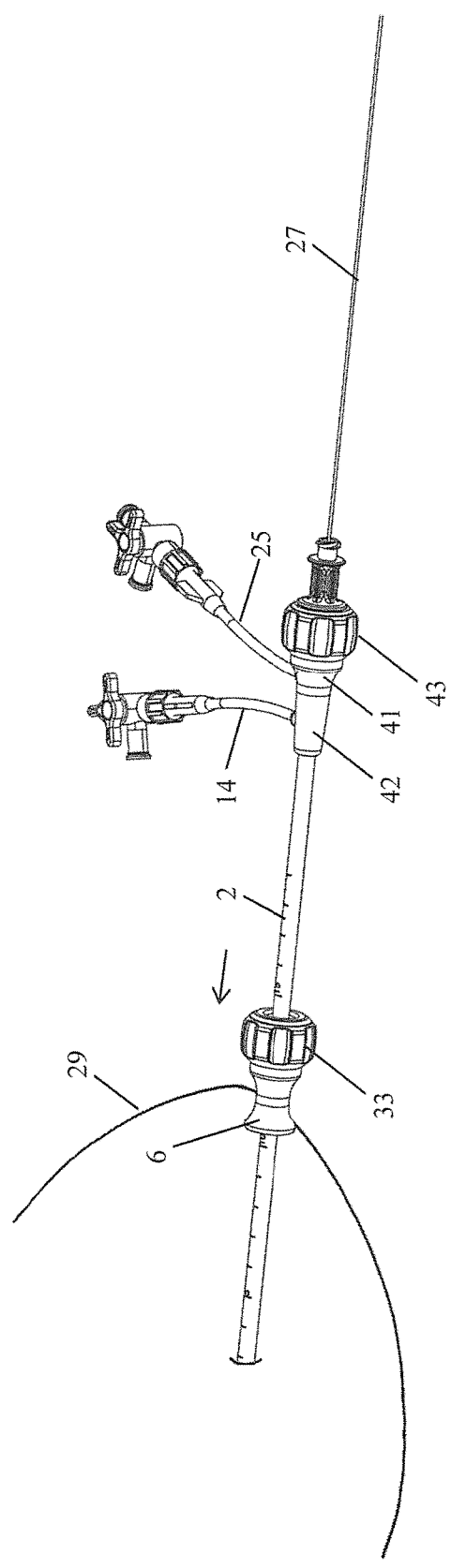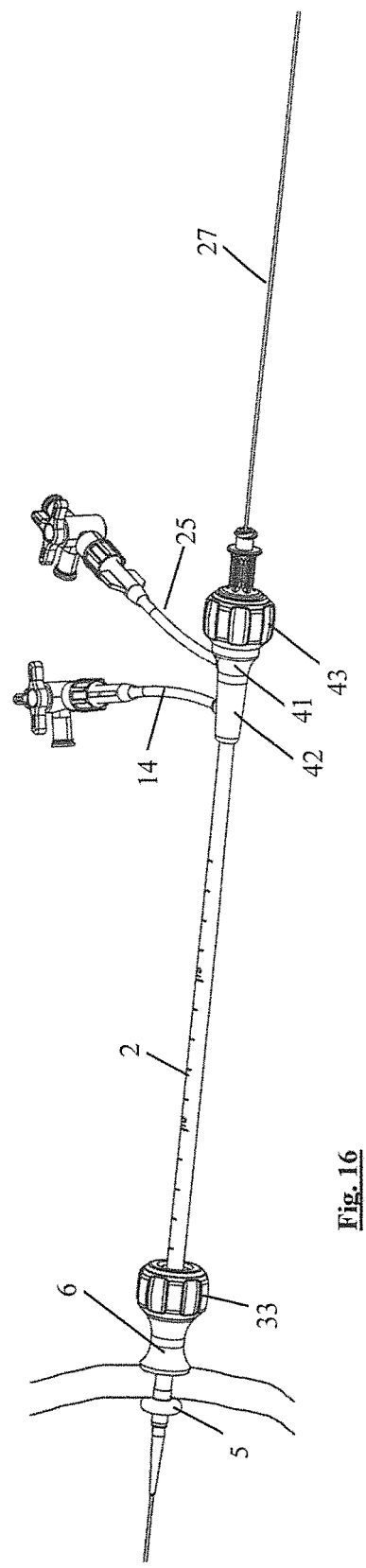
Fig. 15
Fig. 16

INTRODUCER SHEATH

INTRODUCTION

This invention relates to an introducer sheath.

In cardiac procedures where a percutaneous approach is challenging or impossible due to complex anatomy or patient characteristics, a hybrid approach is increasingly used. These procedures utilise a multi-disciplinary team of surgeons and interventional cardiologists where the surgeons provide access, often directly into the heart, and the interventional cardiologist will use this access to introduce devices, stents or valves into the heart without having to stop and fully open the heart. Currently, this access is achieved by using a sheath that is designed for use in the femoral artery.

There are many difficulties that can arise using a standard vascular sheath to access the heart during a hybrid procedure. For example, it is difficult to determine exactly how far inside the heart the sheath is placed. If the sheath is inserted too far it could damage the myocardium which can cause cardiac perforation and potential death. Additionally, during device deployment whilst retracting the sheath, the sheath may migrate out of the heart leading to significant bleeding.

There is a need to provide an alternative to the use of a standard vascular sheath to access the heart during a hybrid procedure.

STATEMENTS OF INVENTION

According to the invention there is provided an introducer sheath comprising:—
- a tubular shaft having a proximal end and a distal end;
- a balloon adjacent to the distal end of the shaft; and
- a proximal anchoring element having a release configuration in which the anchoring element is movable along the shaft and an anchoring configuration in which a tissue bridging gap between the anchoring element and the balloon is reduced and the anchoring element is locked to the shaft.

In one case the anchoring element comprises a collar which is movable along the shaft. The collar, in the release configuration, may be slidably movable along the shaft.

In one case the balloon, on inflation, is configured to buffer the distal tip of the sheath away from tissue.

The balloon may comprise a proximal portion and a distal portion and wherein the proximal portion has a substantially flat proximal face. The distal portion of the balloon may have a substantially convex distal face.

In one case the balloon, on inflation, is generally toroidal shape.

In one case at least the distal portion of the tubular shaft is malleable.

The length of the tubular shaft is typically from 7 cm to 22 cm. The length of the tubular shaft may be from 7 cm to 13 cm. The length of the tubular shaft may be from 7 cm to 11 cm.

The outer diameter of the tubular shaft is typically from 2 mm to 4.667 mm (6 Fr to 14 Fr). The outer diameter of the tubular shaft may be from 2 mm to 3.333 mm (6 Fr to 10 Fr). The outer diameter of the tubular shaft is 2.333 mm (7 Fr).

In one case the anchoring element comprises a collar and a mounting system for mounting the collar to the shaft. The mounting system may comprise a housing, a shaft seal in the housing and first and second hubs parts which retain the housing therebetween, the hub parts being adapted to lock the seal relative to the shaft. In one case the collar is mounted to the housing.

In one case the collar has a distally facing end face that is configured for engaging tissue. The distal end face of the collar may be substantially flat.

In one case the collar is generally frustoconical.

In one case the shaft comprises a distal tip that is softer and/or more flexible than a main body of the shaft.

In another aspect the invention provides an introducer sheath comprising a shaft having a proximal end and a distal end, and a balloon adjacent to the distal end of the shaft. In one case the balloon, on inflation, is configured to buffer the distal tip of the sheath away from tissue.

The introducer sheath further comprises a proximal collar which is movable along the shaft, the collar having an anchored configuration and a release configuration, the collar being movable along the shaft in the released configuration and being configured for anchoring to the shaft in the anchored configuration.

The collar, in the released configuration, may be slidably movable along the shaft.

In one case the balloon and the collar define an adjustable anchoring system for anchoring the shaft to tissue located between the balloon and the collar.

The invention also provides an introducer sheath comprising a tubular shaft having a proximal end and a distal end; and an adjustable anchor for anchoring the shaft to tissue. The adjustable anchor may comprise a balloon at a distal end of the shaft and a proximal collar which is movable along the shaft towards the balloon.

In some cases the shaft comprises a lumen through which fluid is delivered for inflation of the balloon.

In one case the distal tip of the shaft is deflectable and/or malleable.

The distal tip of the sheath may be movable in response to manipulation from a proximal end of the sheath. In one case the sheath comprises control means extending from the distal end to the proximal end of the sheath. The control means may comprise at least one control wire.

In some cases at least a distal portion of the sheath is adapted for deflection in response to input from the proximal end of the sheath.

In one case at least a distal portion of the sheath is of braided construction.

The shaft may comprise marking to indicate the depth of insertion.

The invention also provides a hybrid method for accessing a heart comprising the steps of:—
- providing an introducer sheath having a shaft and a balloon at the distal end of the shaft; making an opening to provide an access point into the heart;
- with the balloon in a deflated configuration, inserting a distal portion of the introducer sheath through the incision;
- inflating the balloon to provide a safety bumper at the distal end of the sheath; and carrying out a procedure by passing devices through the sheath.

In another aspect, the invention also provides a hybrid method for accessing a heart comprising the steps of:—
- providing an introducer sheath having a shaft, a balloon at the distal end of the shaft and a collar proximal of the balloon;
- making an opening to provide an access point into the heart;
- with the balloon in a deflated configuration, inserting a distal portion of the introducer sheath through the incision;
- inflating the balloon;
- advancing the collar towards the balloon;

locking the collar in a desired position on the shaft; and
carrying out a procedure by passing devices through the sheath.

The making of the opening may comprise:—
inserting a needle through the wall of the heart;
extending a dilator beyond the distal end of the introducer sheath to enlarge the opening made by the needle;
removing the needle;
inserting a guidewire through the opening; and
removing the dilator.

In one case the procedure comprises deploying a stent in the right ventricular outflow tract.

In another case the procedure comprises deploying a stent in a branch pulmonary artery.

In a further case the procedures comprise closing a ventricular septal defect.

The procedure may comprise closure of a paravalvular leak.

In one case the procedure involves manipulation of a heart valve, such as balloon dilation of a stent-valve.

The invention also provides a method for accessing a site of interest comprising the steps of:—
providing an introducer sheath having a shaft and a balloon at the distal end of the shaft; with the balloon in a deflated configuration, inserting the introducer sheath through an access point; and
inflating the balloon to provide a safety bumper at the distal end of the sheath.

A method for accessing a site of interest may comprise the steps of:—
providing an introducer sheath having a shaft and a balloon at the distal end of the shaft; with the balloon in a deflated configuration, inserting the introducer sheath through an access point; and
inflating the balloon to provide a safety bumper at the distal end of the sheath.

A method for accessing a site of interest may comprise the steps of:—
providing an introducer sheath having an adjustable anchor for anchoring the shaft to tissue;
inserting the sheath through an access point; and
deploying the anchor to anchor the shaft to tissue.

Also provided is a method for accessing a site of interest comprising the steps of:—
providing an introducer sheath comprising a tubular shaft having a proximal end and a distal end, a balloon adjacent to the distal end of the shaft and a collar which is located proximally of the balloon;
with the balloon in a deflated configuration, inserting the introducer sheath through an access point;
inflating the balloon on one side of an opening in tissue;
moving the collar along the shaft towards the balloon to engage an opposite side of the tissue opening; and
anchoring the collar to the shaft to anchor the sheath to the tissue.

The method may comprise the step of controlling deflection of a distal end of the sheath.

In some cases the site of interest is a heart.

The method in some cases comprises the step of creating an incision to provide the access point through which the sheath is introduced.

Also provided is a hybrid method for accessing a heart comprising the steps of:—
providing an introducer sheath having a shaft and a balloon at the distal end of the shaft;
making an incision to provide an access point into the heart;
with the balloon in a deflated configuration, inserting the introducer sheath through the incision;
inflating the balloon to provide a safety bumper at the distal end of the sheath; and
carrying out a procedure by accessing through the sheath.

BRIEF DESCRIPTION OF THE DRAWINGS

The invention will be more clearly understood from the following description thereof, given by way of example only, in which:
FIGS. 14 and 15 are views illustrating a collar being advanced along the shaft of the introducer sheath;
FIG. 16 illustrates the introducer sheath with a wall of the heart between an inflated distal balloon and the collar.

DETAILED DESCRIPTION

Figure 1:
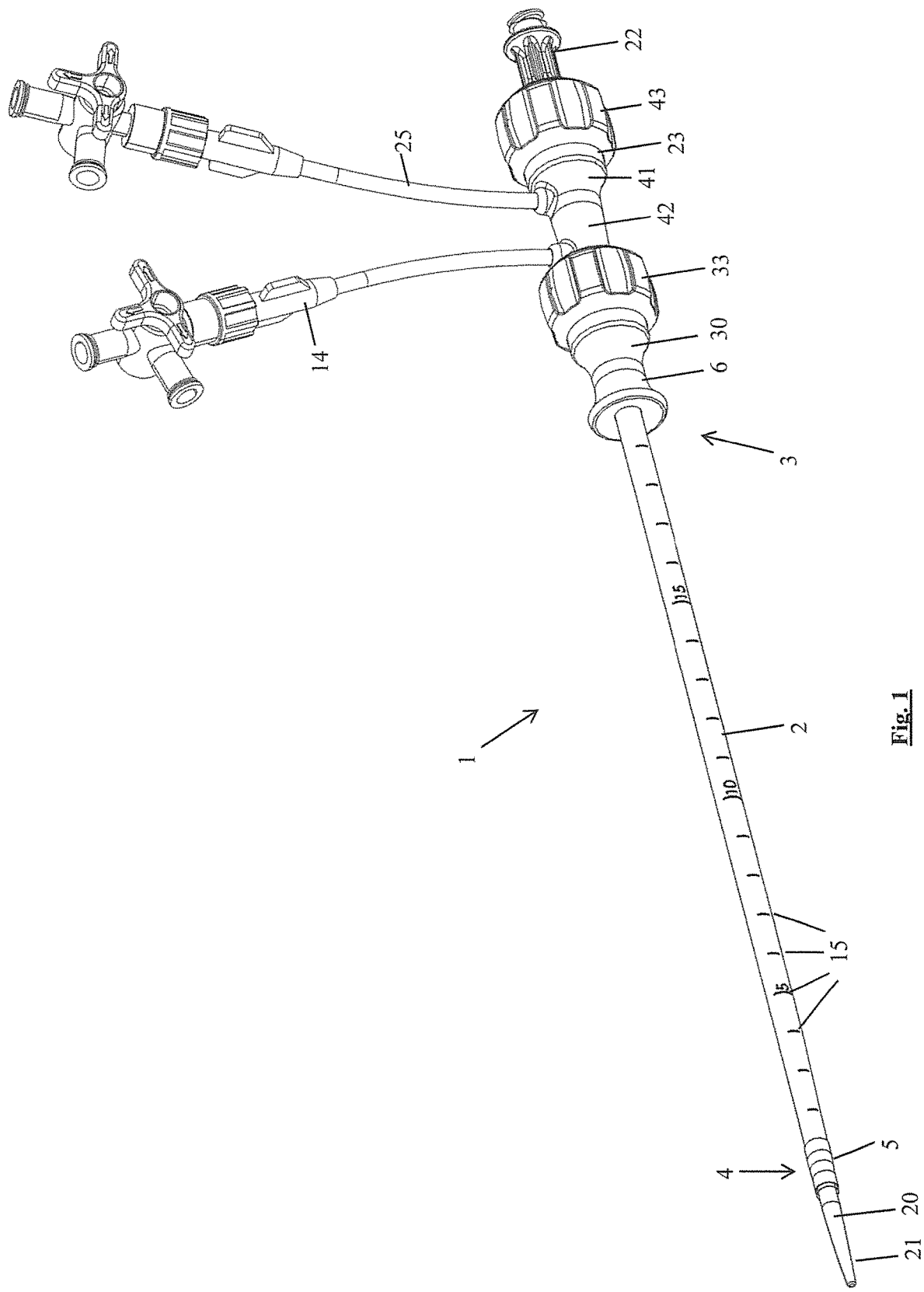
—
FIG. 1 is a perspective view of an introducer sheath according to the invention.
Figure 2:
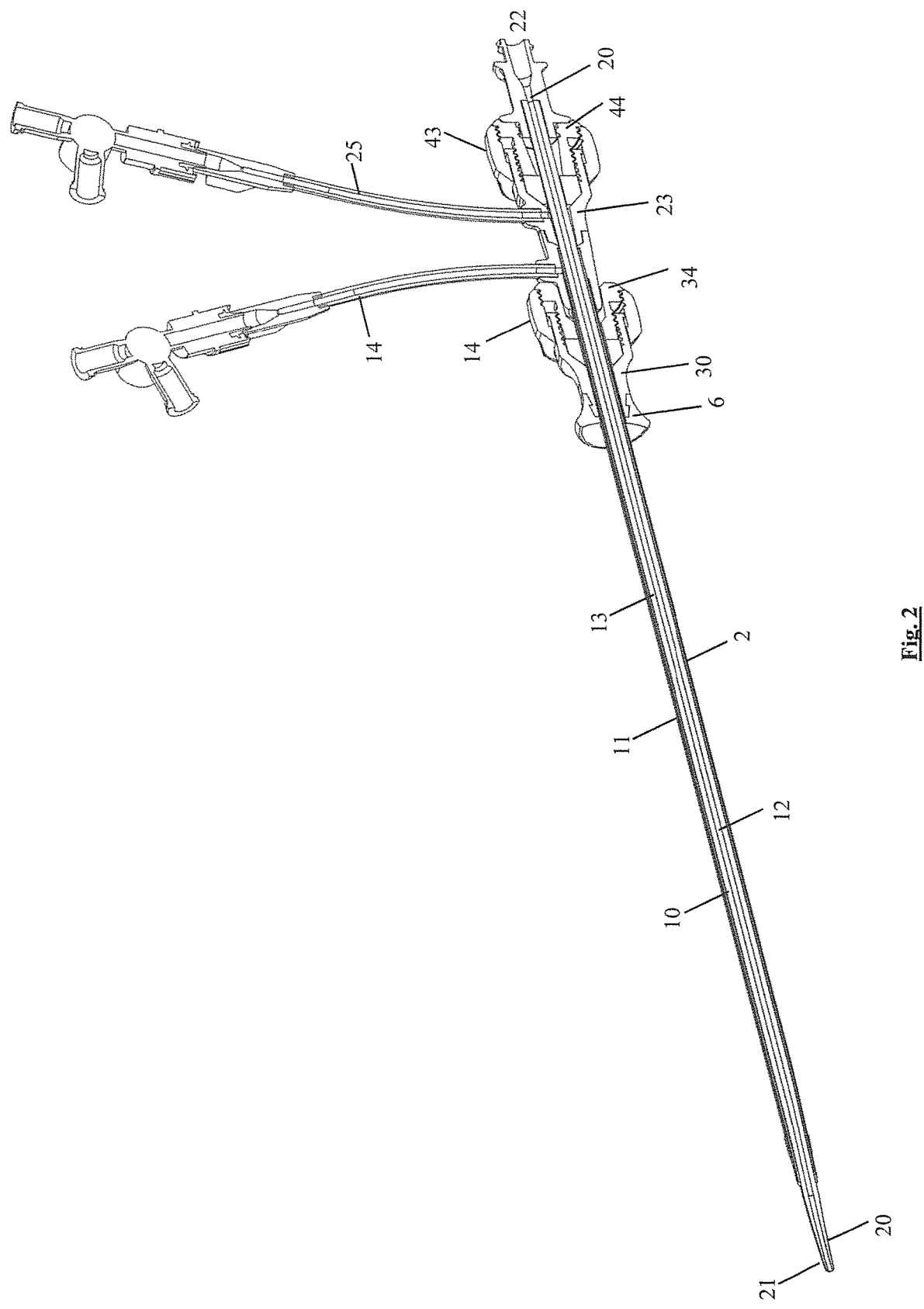
FIG. 2 is a cross sectional view of the introducer sheath of FIG. 1.
Figure 3:
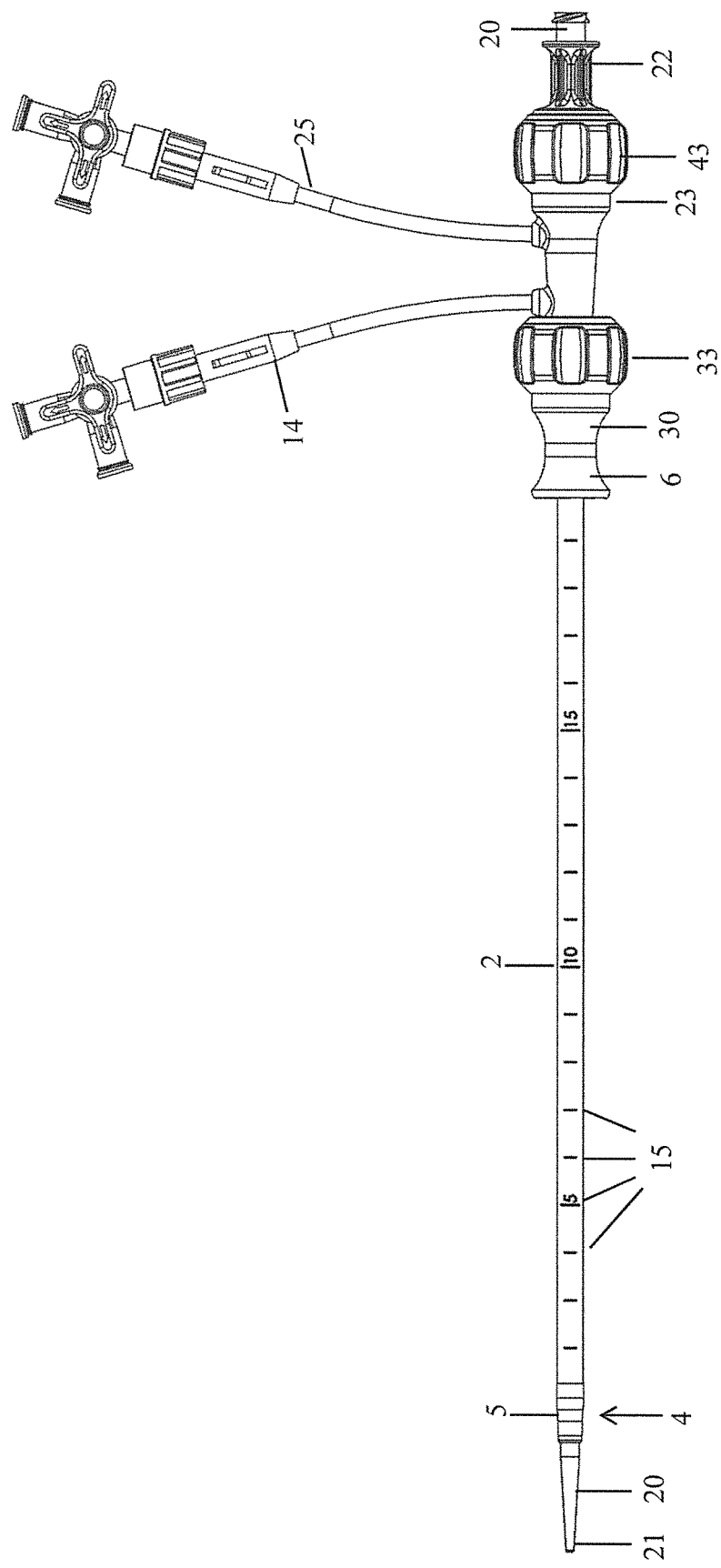
FIG. 3 is a side view of the introducer sheath.
Figure 4:
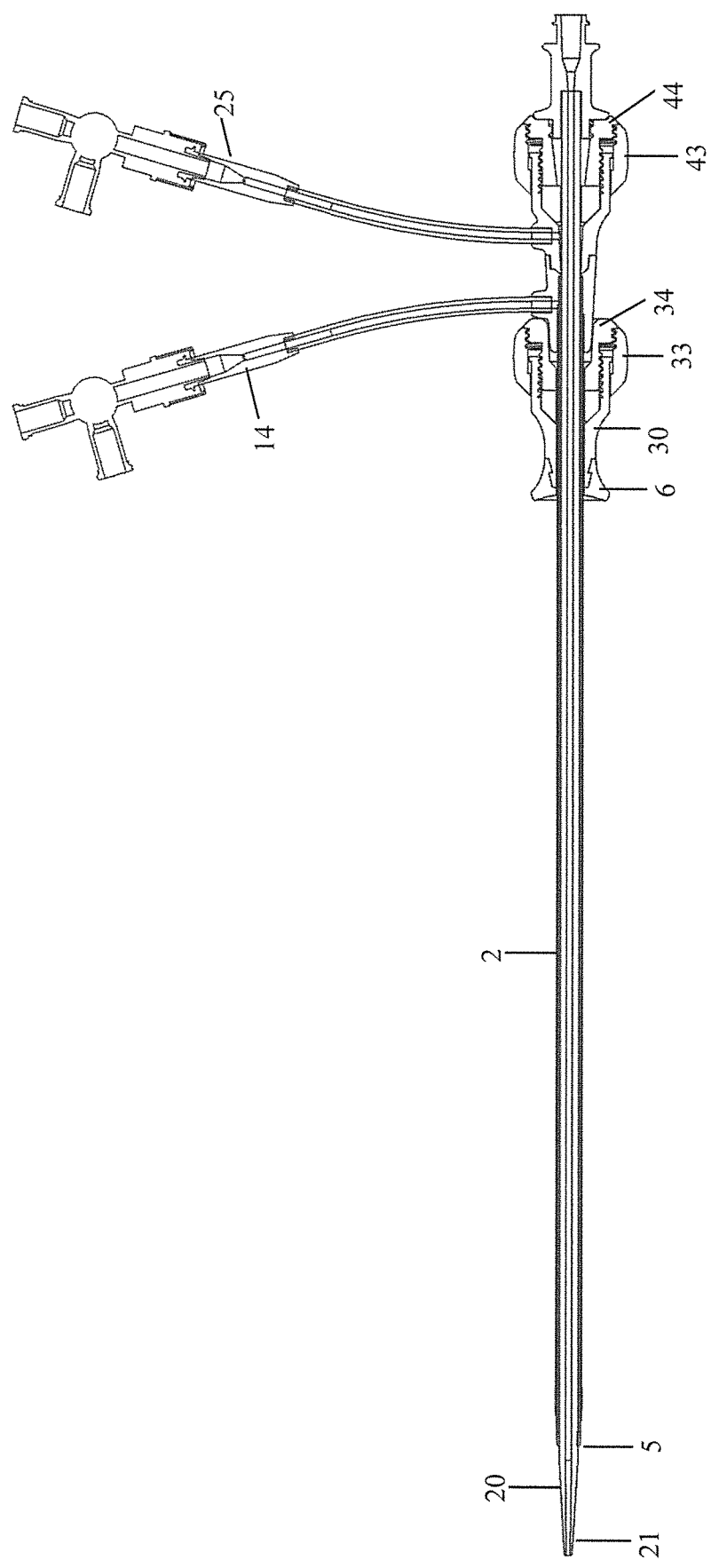
FIG. 4 is a cross sectional view of the introducer sheath of FIG. 3.

The invention provides an apparatus and method for improving patient safety and outcomes in the vasculature during hybrid cardiac procedures by reducing or eliminating the potential for damaging tissue, for example, on the walls of the heart.

The invention provides an introducer sheath for use during hybrid procedures for insertion directly into the tissue of the heart or the major arteries. The sheath will include markings on the outer lumen of the sheath that will be visible to both the naked eye and under fluoroscopy. This will aid in controlling the depth of insertion into the heart. They will also be visible under fluoroscopy which will help with accurate manipulation of the sheath.

The distal end of the sheath will have a small fixing balloon. The balloon will inflate to a low pressure and extend close to, or beyond, the tip when inflated. This will protect from inadvertent tip damage to the tissue of the heart and reduce the risk of inadvertent sheath prolapse.

The inner layer of the sheath will be smooth to allow smooth passage of treatment devices through the sheath.

A deflectable tip may be used to facilitate guidance of the sheath tip towards the area of interest, providing a more direct approach for device delivery.

Referring to the drawings and initially to FIGS. 1 to 18, there is illustrated an introducer sheath 1 according to the invention comprising a shaft 2 having a proximal end 3 and a distal end 4. A balloon 5 is mounted adjacent to the distal end 4 of the shaft 2. The introducer sheath also comprises a proximal anchoring element, in this case a collar 6 which is movable, such as slidably movable, along the shaft 2.

The shaft has an inner wall 10 and an outer wall 11. The inner wall 10 defines an inner lumen 12 which is smooth to facilitate ease of insertion of various devices through the sheath. The shaft 2 has an inflation lumen in communication with the balloon 5. In this case the inflation lumen is provided by a space 13 between the inner and outer shaft walls 10, 11. Fluid such as air or saline is delivered through the inflation lumen 13 to inflate and deflate the balloon 5 through a side port 14, as required, during a procedure. The balloon 5 has a proximal waist portion 7 that is attached, for example by adhesive bonding, to the shaft outer wall 11 and a distal waist portion 8 that is attached to shaft inner wall 11 and to the distal tip 9.

The shaft 2 has markings 15 along at least a portion of the length of the shaft to provide an indicator to the clinician of the depth to which the shaft has been inserted. The shaft may also have suitably placed radiopaque marker bands such as a distal marker band 19.

The shaft is of a suitable material such as a thermoplastic elastomer (polyether block amide) made from flexible polyether and rigid polyamide such as PEBAX® available in different grades from Arkema and has a soft flexible tip 9 of a suitable material such as a softer grade of PEBAX® than that of the main body of the shaft.

In some embodiments the introducer sheath is of a diameter and length that has been found suitable for use in procedures on infants and small children. The shaft is preferably 7 Fr or 8 Fr and the length is from 7 cm to about 11 cm. The maximum diameter of the balloon, when inflated, is typically 10 mm and the length of the inflated portion is about 5 mm. The balloon may be of a suitable material such as latex or polyurethane.

The shaft may comprise a suitable liner such as HDPE (high density polyethylene) or PTFE (polytetrafluoroethylene). The shaft outer may be of any suitable material such as PEBAX®, for example, grade 7233. The inner overcoat may be of any suitable material such as PEBAX®, for example grade 3555. The distal tip may be of a softer/more flexible grade material such as PEBAX® 3533. For improved performance such as kink resistance, the shaft may be reinforced along at least portion of the length thereof by a coiled reinforcement wire. The marker bands may be of a suitable radiopaque material such as platinum (Pt) or tantalum (Ta).

In some of the drawings a dilator 20 having a distal end 21 and a proximal end 22 is illustrated extending through the shaft 2. The introducer sheath in some cases may have a proximal hub seal assembly 23 to facilitate insertion and sealing of the dilator 20. The hub seal assembly 23 has a side port 25 to facilitate flushing of the introducer shaft. A guidewire 27 is also illustrated in some of the drawings passing through a hole 28 in a wall of a heart 29.

Figure 5:
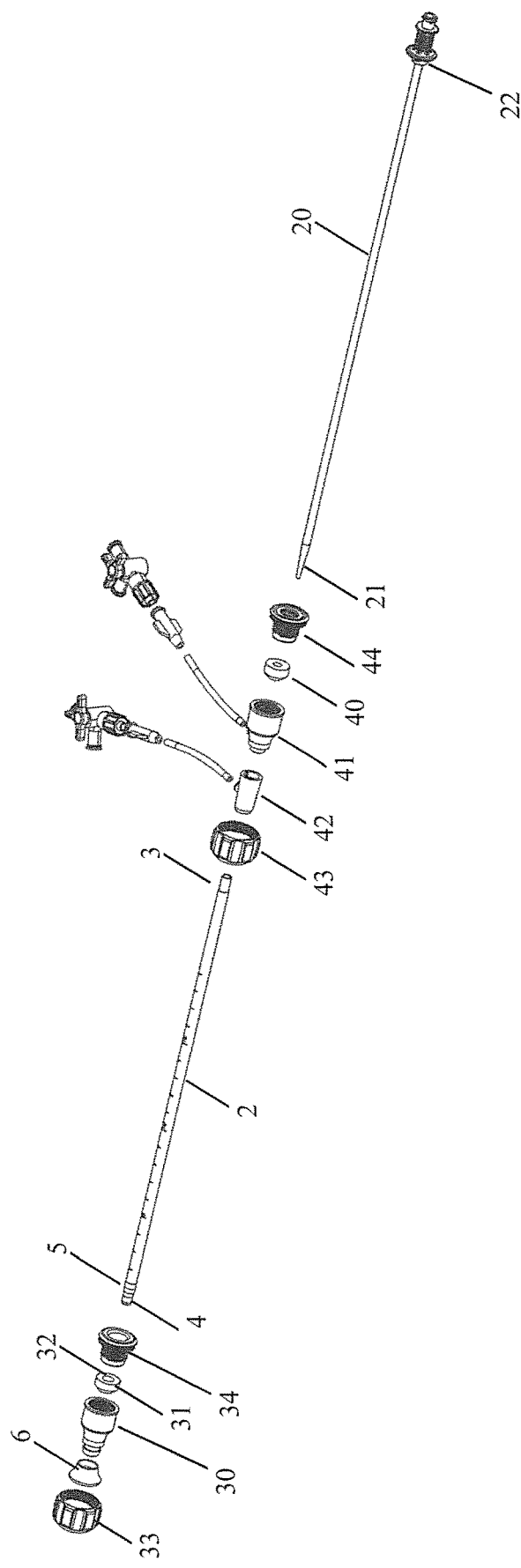
FIG. 5 is an exploded view of the introducer sheath.
Figure 6:
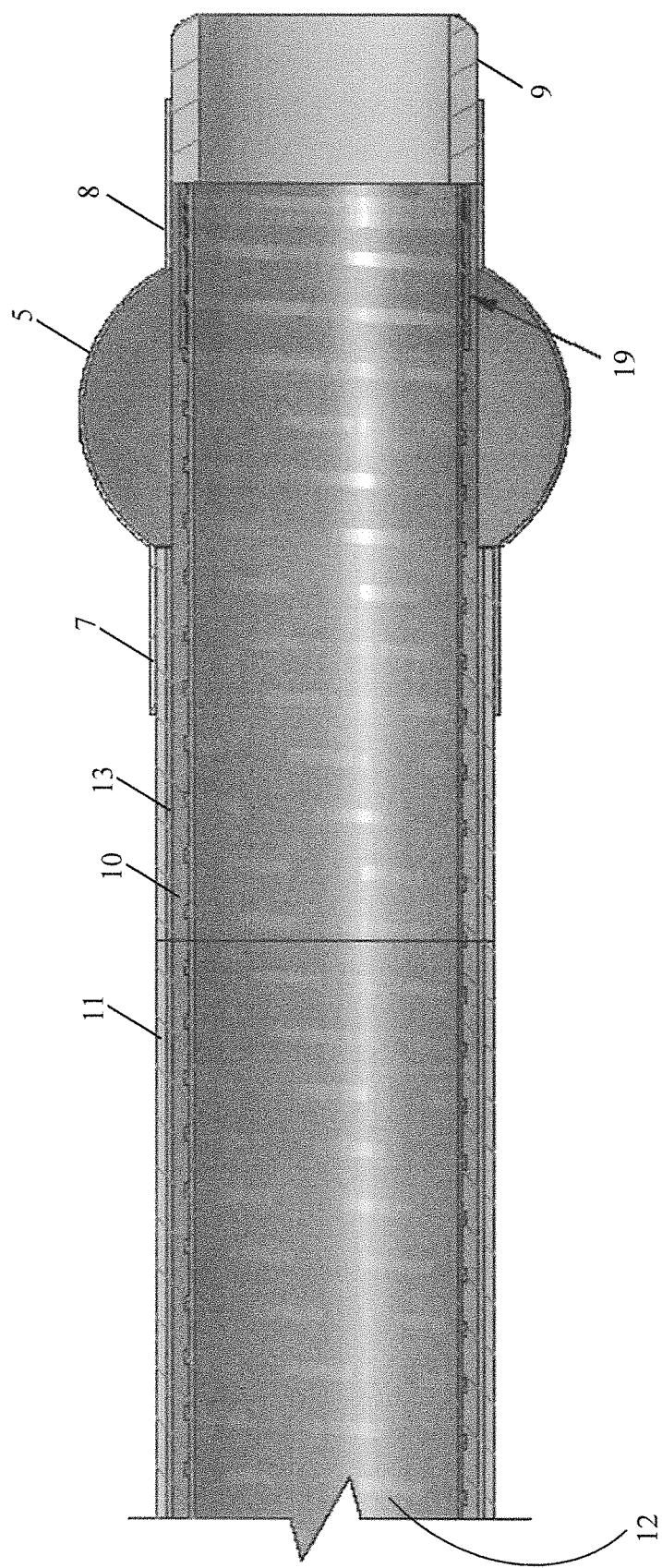
FIG. 6 is an enlarged cross sectional view of a distal end of the introducer sheath.
Figure 7:
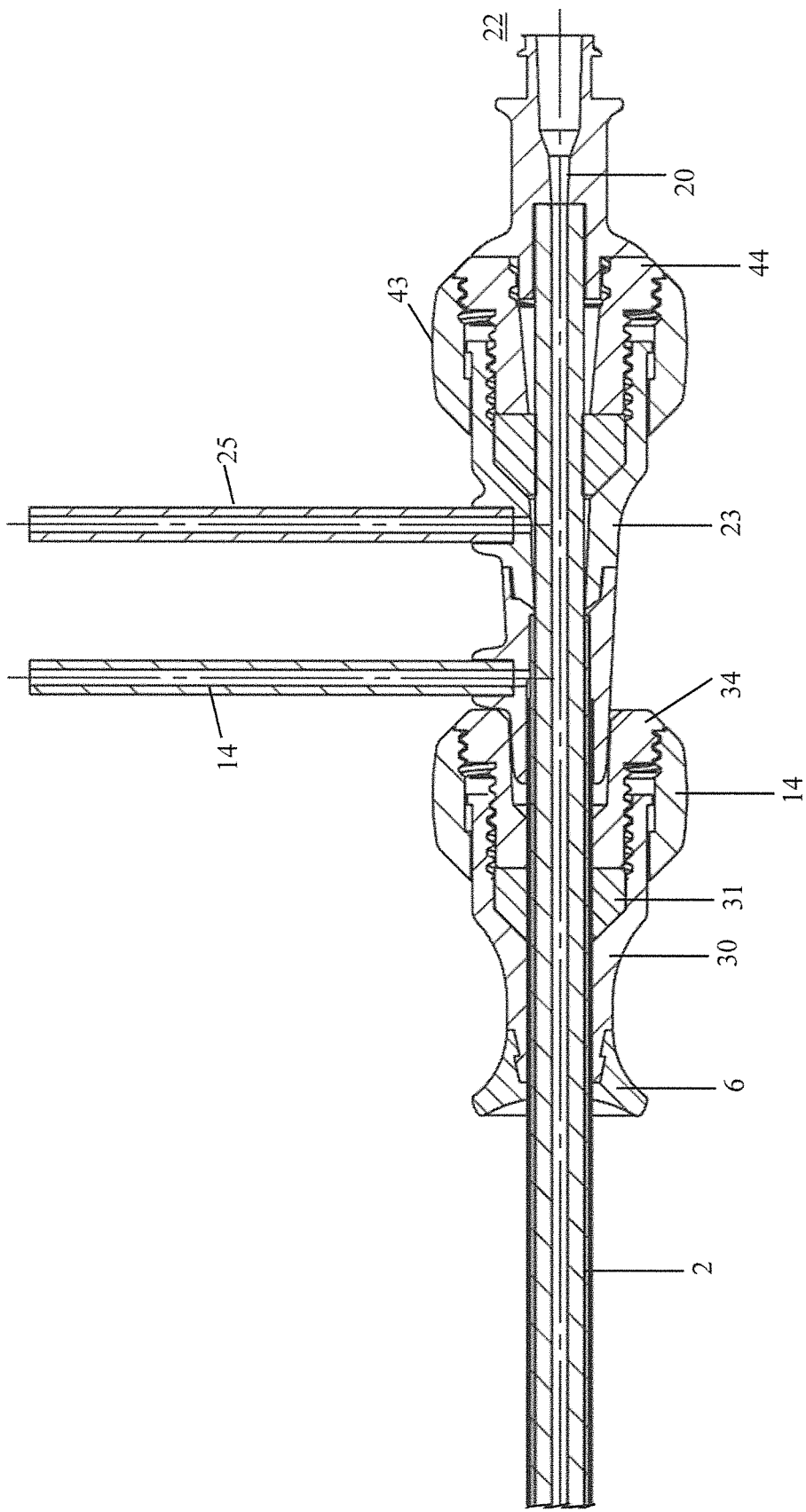
FIG. 7 is an enlarged cross sectional view of a proximal end of the introducer sheath.
Figure 8:
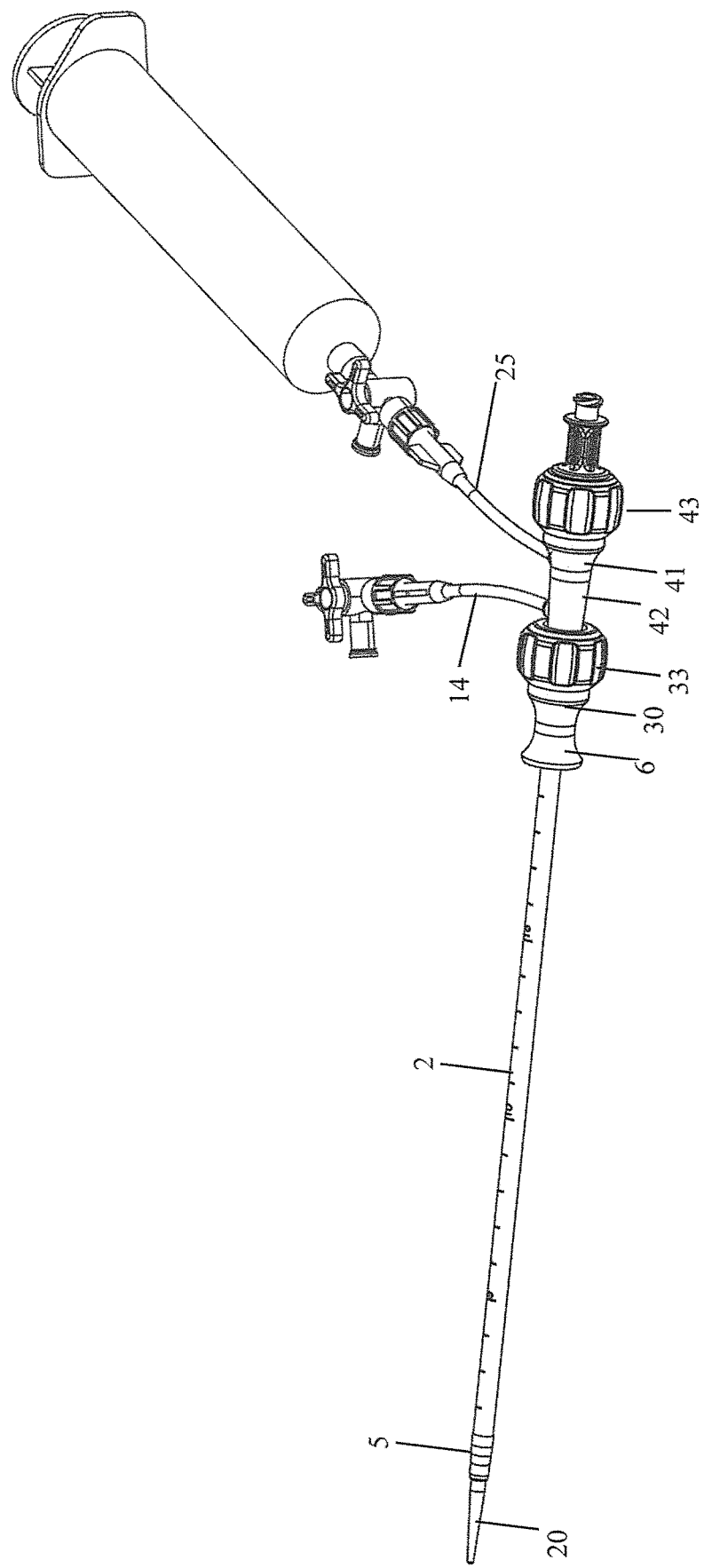
FIG. 8 is a view of the introducer sheath during flushing.
Figure 9:
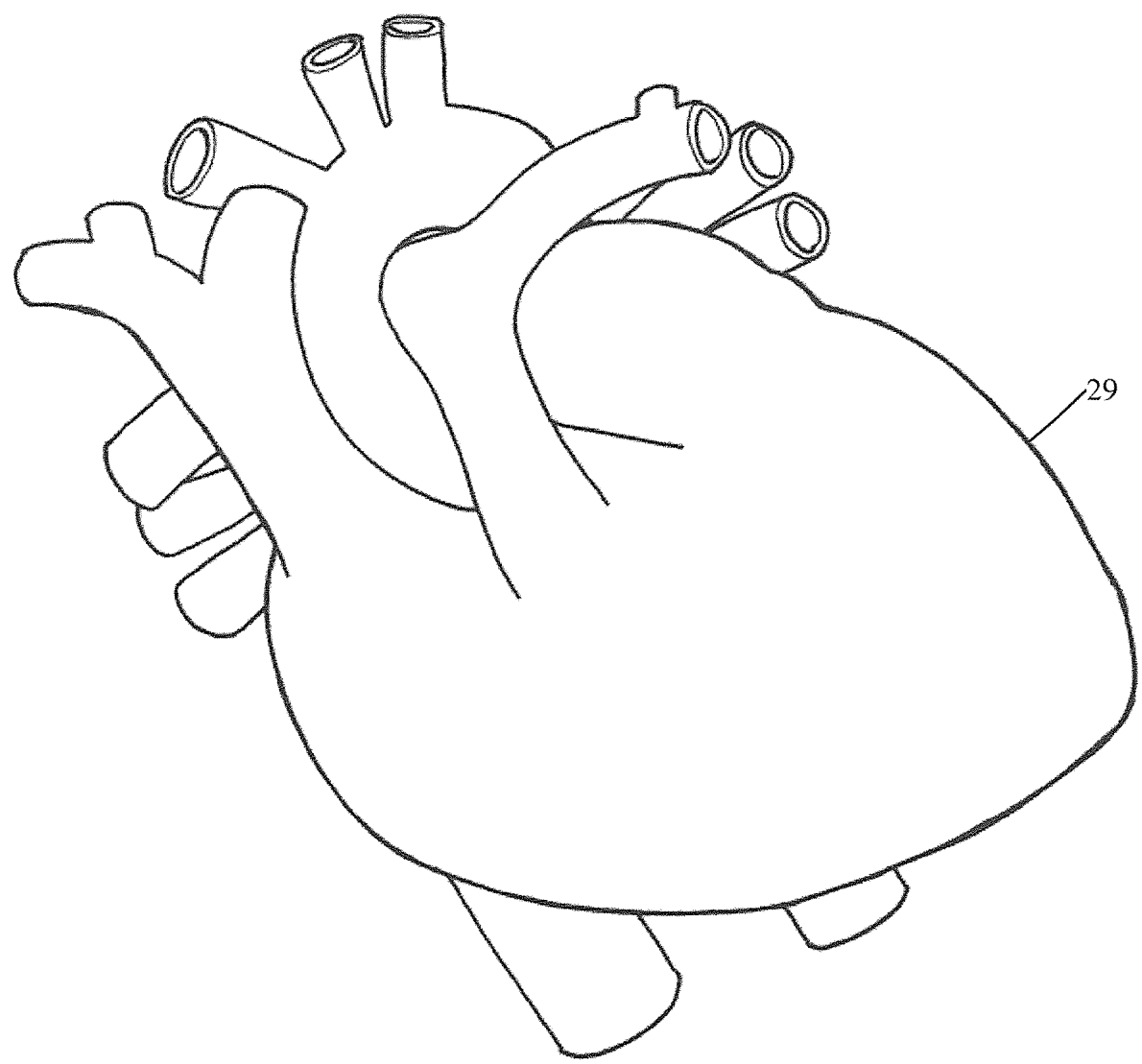
FIG. 9 is a diagram of a heart.

Referring in particular to FIG. 5, the various parts of the introducer sheath are illustrated in a disassembled form. The dilator 20 is also shown in this drawing.

The collar 6 is mounted to a housing 30, for example, by adhesive bonding. Alternatively, the collar 6 may be integral with the housing. However, it is preferred that the collar 6 is of a different material than that of the housing, preferably of a softer material such as a soft silicone or rubber that, in use, will be engaged with a delicate wall of the heart.

A seal 31 having a through hole 32, through which the shaft 2 extends, is mounted in the housing. The seal 31 is of a relatively pliable material to facilitate a degree of deformation of the seal. The housing 30 is retained between hub parts 33, 34 which are movable relative to one another to cause the seal 31 to be deformed for locking the housing 30 and the seal 31 to the shaft 2. The assembly of the collar 6, the housing and seal 30, 31 and the hub parts 32, 33 facilitates sliding movement of the assembly along the shaft when the engagement between the hub parts 33, 34 is loosened. The collar 6 moves with the assembly and in this way the collar can be advanced along the shaft 2 until the distally facing end of the collar 6 is engaged with the tissue wall.

In one case, the introducer sheath includes an interlock to provide a mechanical and/or tactile and/or audible feedback to the clinician to prevent over-tightening of the seal 31.

The introducer sheath has fittings at the proximal end to facilitate sealing engagement with shafts of various devices inserted at the proximal end. The proximal fittings comprise a seal 40, a first housing part 41 for the seal 40, a second housing part 42 and hub parts 43, 44 which engage with the housing parts 41, 42 to deform the seal 40 for sealing engagement with a shaft extending therethrough. One such shaft is the shaft of the dilator 20. The proximal hub parts 43, 44 are loosened to facilitate insertion and removal of a shaft and are tightened to form a haemodynamic seal with a shaft inserted through the seal.

Figure 10:
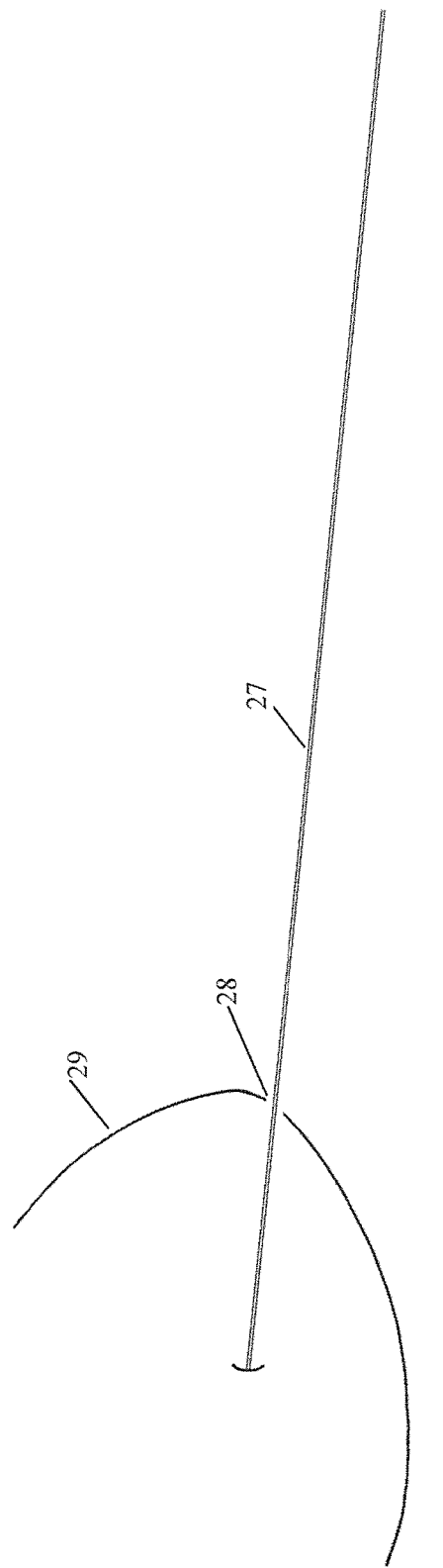
FIG. 10 is a view of a guidewire being inserted through a hole in the heart wall.

FIG. 10 shows a guidewire 27 being inserted through a hole 28 ion the heart wall 29.

Figure 11:
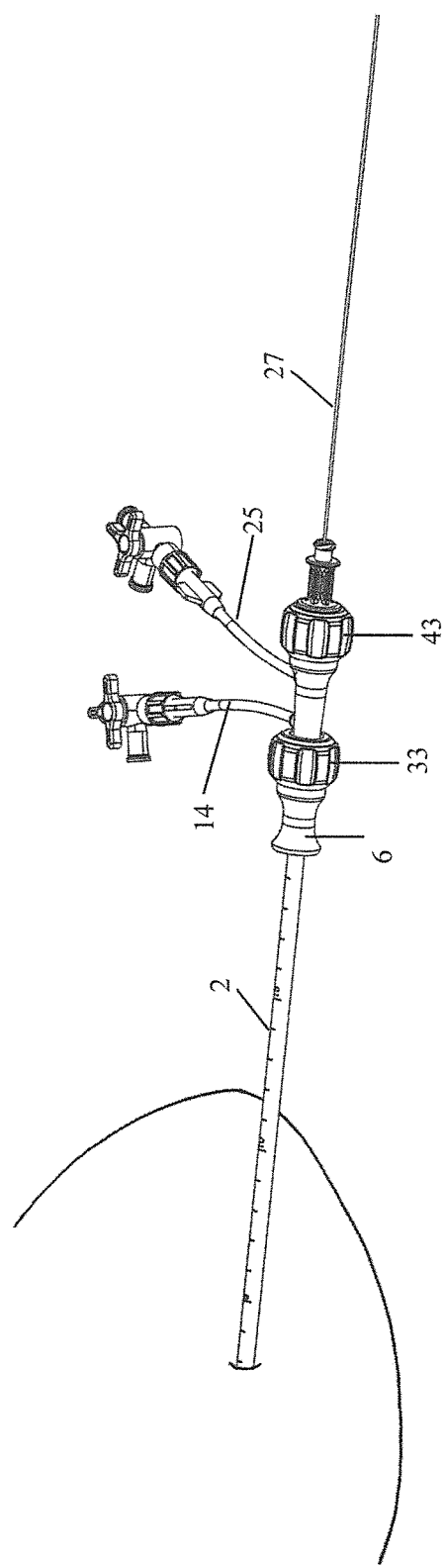
FIG. 11 shows the introducer sheath being advanced along the guidewire.

FIG. 11 shows the introducer sheath being advanced along the guidewire 27.

Figure 12:
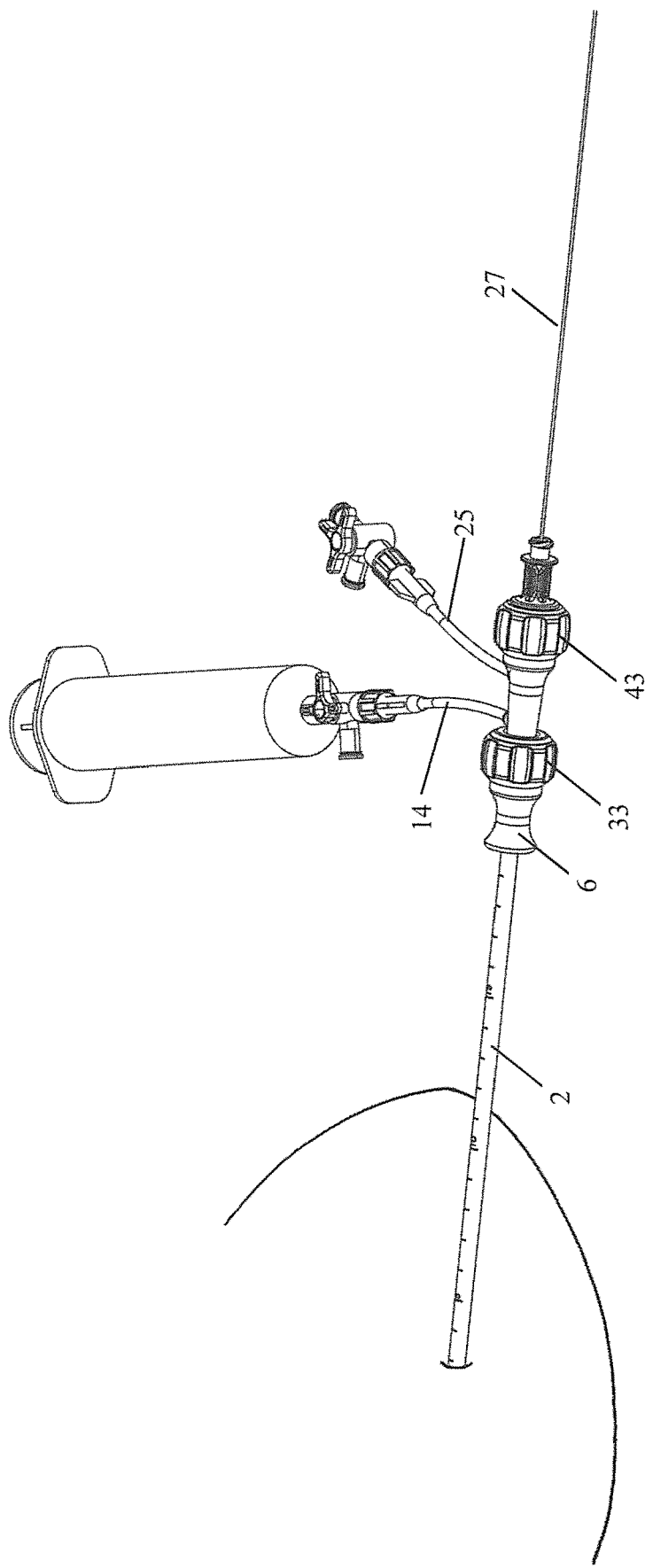
FIG. 12 shows the inflation of a distal balloon of the introducer sheath from the proximal end.

FIG. 12 shows the inflation of the distal balloon 5 of the introducer sheath from the proximal end.

Figure 13:
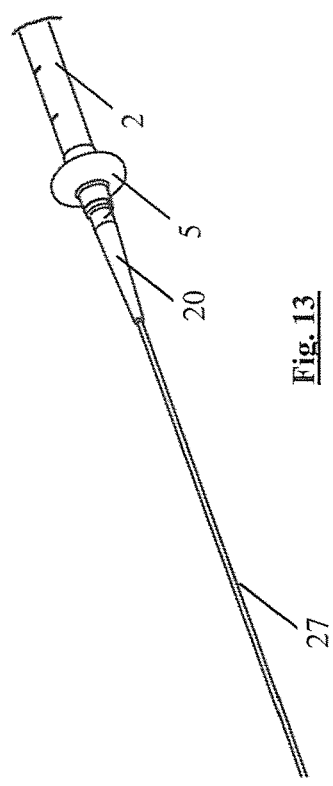
FIG. 13 illustrates the distal end of the introducer sheath with the balloon inflated.

FIG. 13 illustrates the distal end of the introducer sheath with the balloon 5 inflated.

Figure 14:
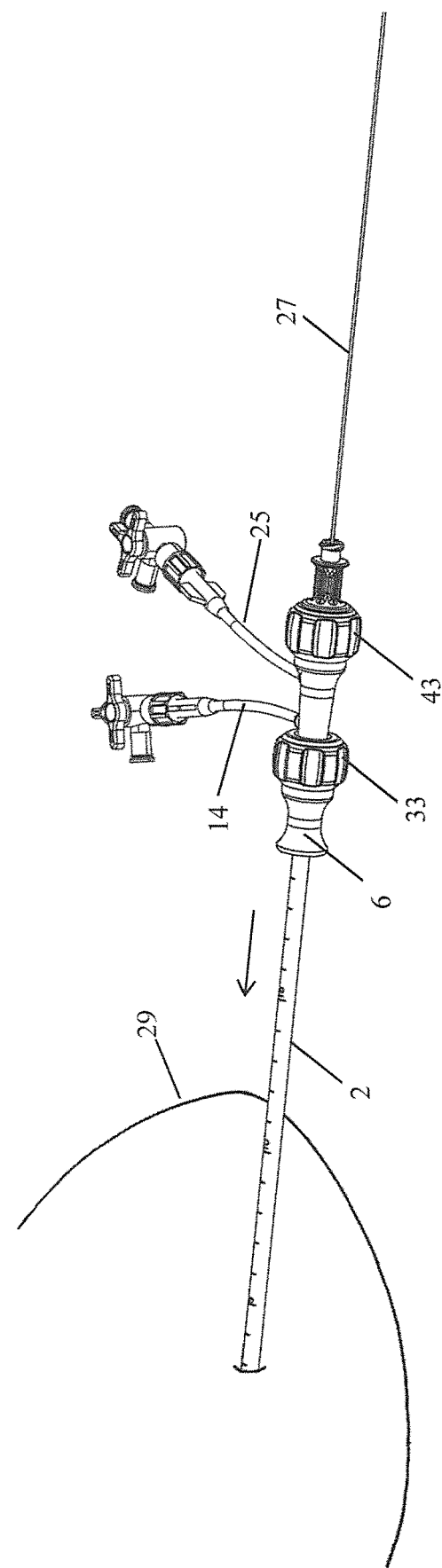

FIGS. 14 and 15 are views illustrating the collar 6 being advanced along the shaft 2 of the introducer sheath.

FIG. 16 illustrates the introducer sheath with a wall of the heart 29 between an inflated distal balloon 5 and the collar 6. This ensures that the introducer sheath is secured in position and thus facilitates procedures to be carried out by introducing and/or removing through the introducer sheath.

Figure 17:
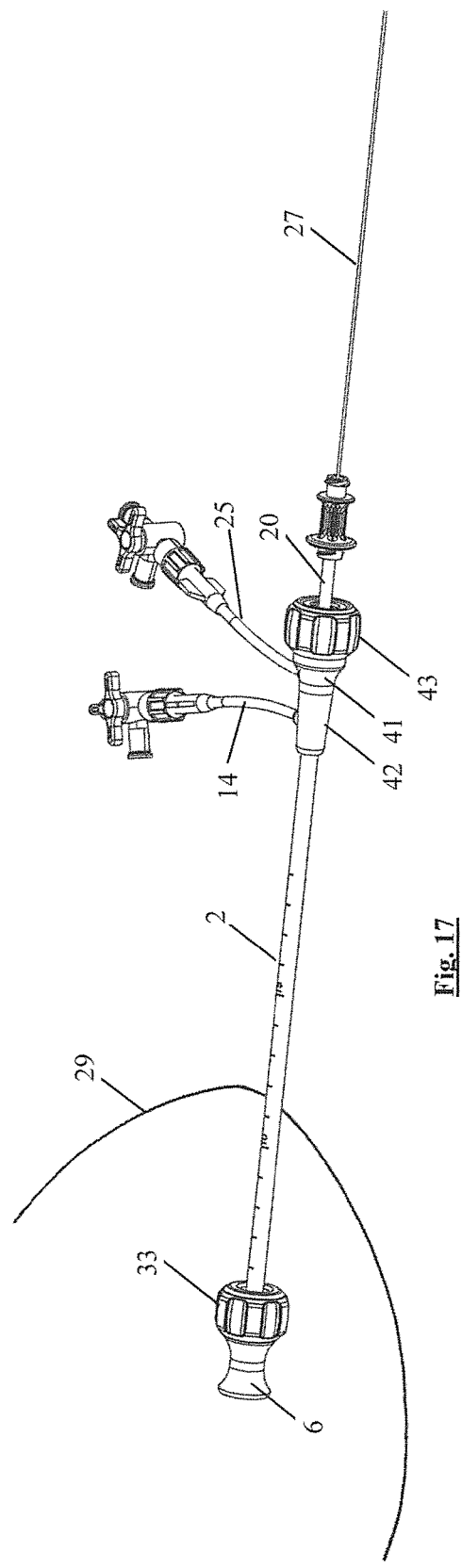
FIG. 17 illustrates removal of a dilator from the introducer sheath.

FIG. 17 illustrates removal of the dilator 20 from the introducer sheath.

Figure 18:
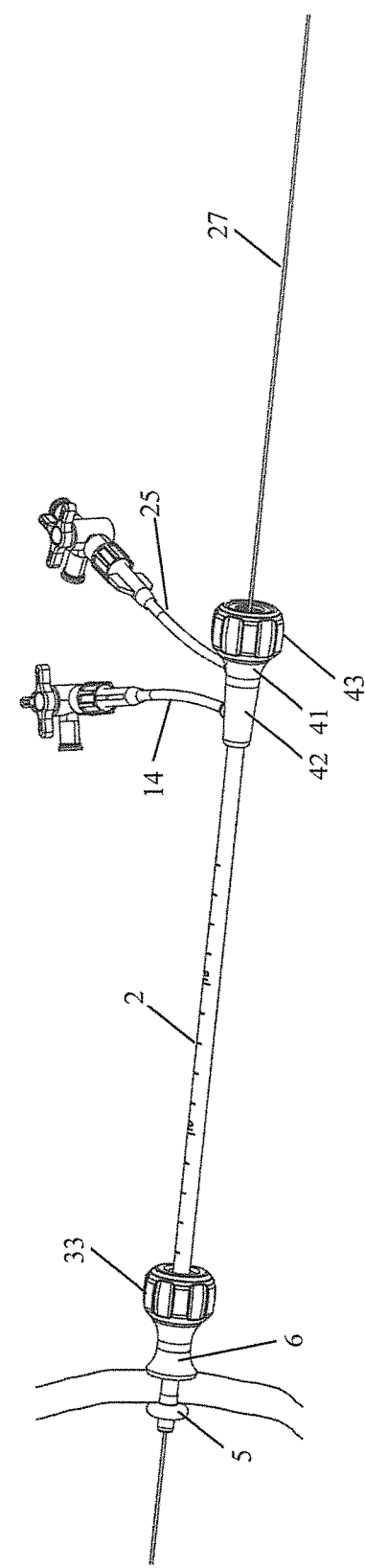
FIG. 18 shows the introducer sheath in position with the dilator removed.
Figure 19:
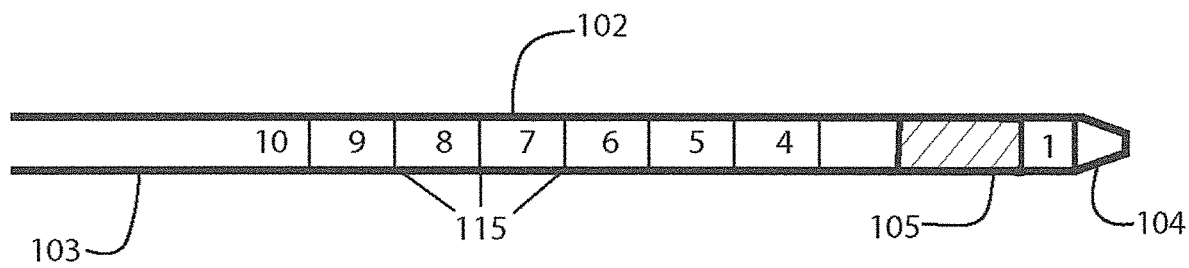
FIG. 19 is an illustration of portion of a shaft of another introducer sheath according to the invention.
Figure 20:
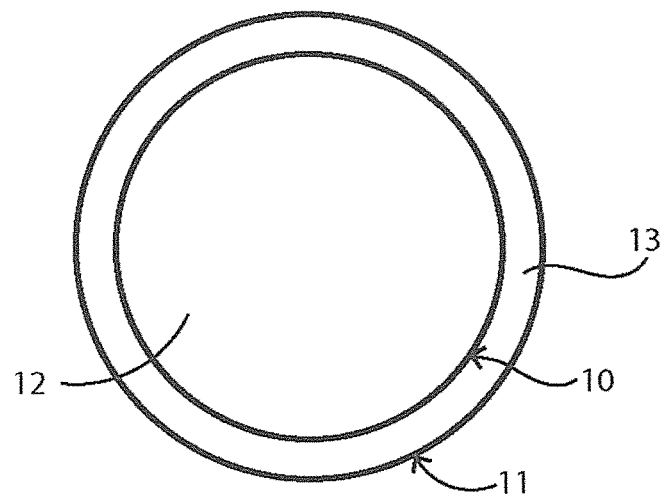
FIG. 20 is a cross sectional view of the shaft of FIG. 17.

FIG. 18 shows the introducer sheath in position with the dilator 20 removed.

Referring to FIGS. 19 to 25 an introducer sheath 100 comprises a shaft 102 having a proximal end 103 and a distal end 104. A balloon 105 is mounted adjacent to the distal end 104 of the shaft 102. On inflation, the balloon 105 is, in this case, configured to buffer the distal tip of the sheath away from tissue.

The shaft comprises an inner wall 110 and an outer wall 111. The inner wall 110 defines an inner lumen 112 which is smooth to facilitate ease of insertion through the sheath. The shaft 102 has an inflation lumen in communication with the balloon 104. In this case the inflation lumen is provided by a space 113 between the inner and outer walls 110, 111. Fluid is delivered through the inflation lumen 113 to inflate and deflate the balloon, as required, during a procedure.

The shaft comprises markings 115 along at least portion of the length of the shaft 102 to provide an indicator to the clinician of the depth to which the shaft has been inserted.

In some cases the distal tip of the sheath is deflectable. This may be achieved in a number of different ways. For example, the clinician may control the deflection of the tip from the proximal end of the introducer sheath. One way of achieving this is to provide control wire 120 (see FIG. 23) which extend from the distal end of the sheath to the proximal end. The clinician manipulates the wires at the proximal end to control the movement of the distal tip. To facilitate such control, the distal tip of the sheath may be of a malleable construction. For example, the distal tip may comprise a braided construction 121 which may be coated with a hydrophilic coating 122.

The introducer sheath is adapted to allow other devices such as catheters, diagnostic devices, or treatment devices to travel through the sheath to a desired location. The smooth inner lumen 112 allows for the devices, drugs etc., to be delivered. Indicator markers 115 will allow the clinician to know exactly how far inside the heart the distal tip of the sheath is inserted. During introduction, the balloon 105 is flush with the outer diameter of the sheath. The inner lumen 112 of the sheath is smooth.

Figure 21:
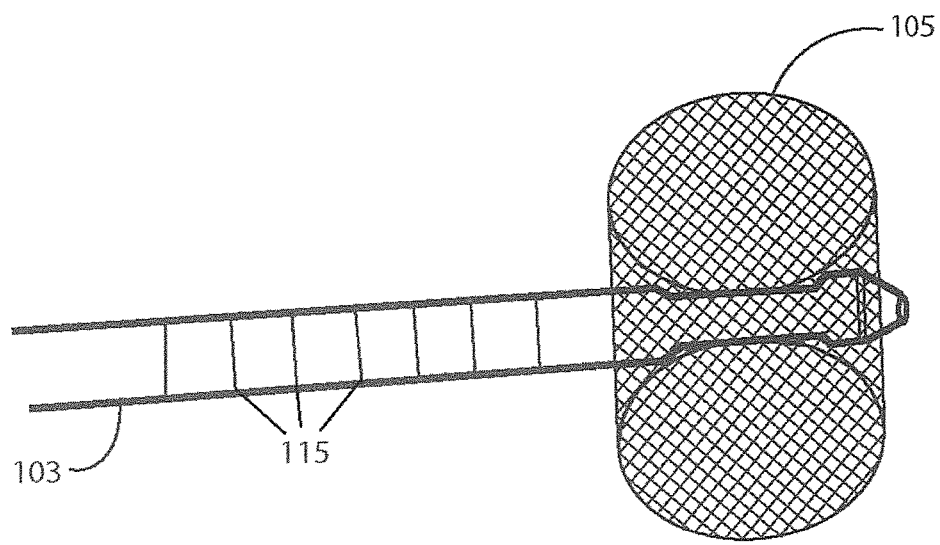
FIG. 21 is an illustration of a distal portion of the sheath with a distal balloon inflated.

FIG. 21 shows the sheath 101 with the protective balloon 105 inflated from above.

Figure 22:
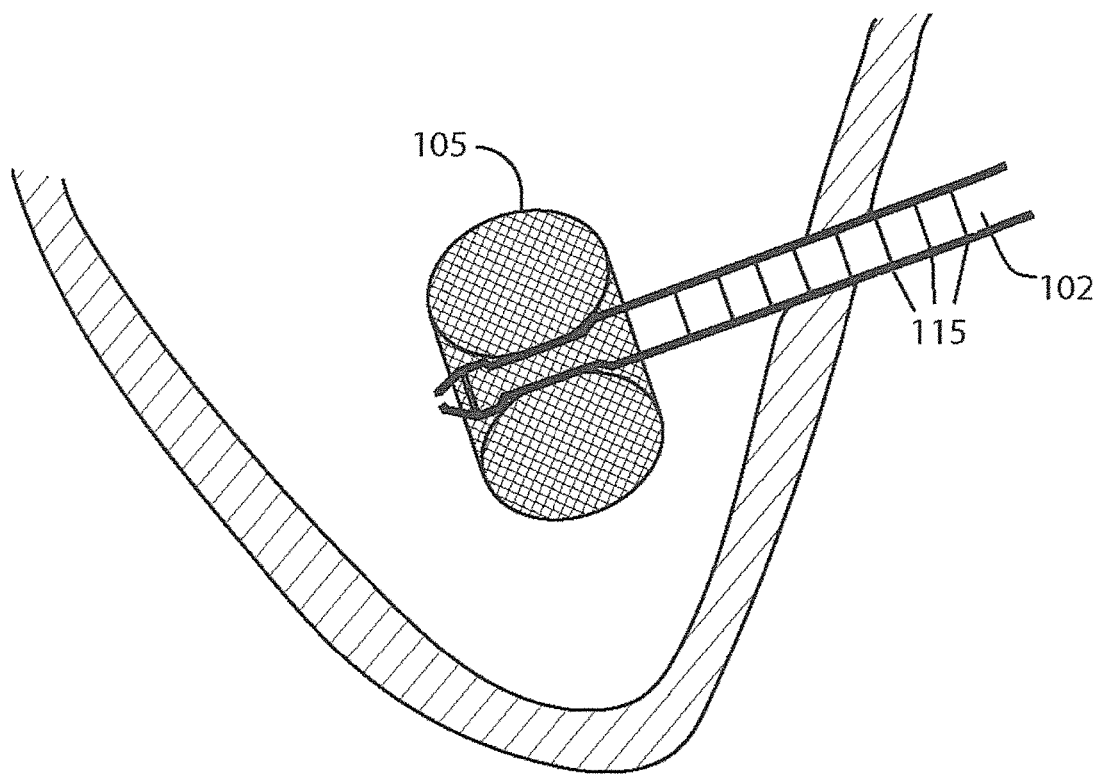
FIG. 22 is an illustration of the introducer sheath, in use.

FIG. 22 shows distal ends of the sheath inserted into the ventricle during a procedure. The balloon 105 is inflated to protect the patient from tip damage and the markings 115 allow accurate placement and manipulation of the sheath.

Figure 23:
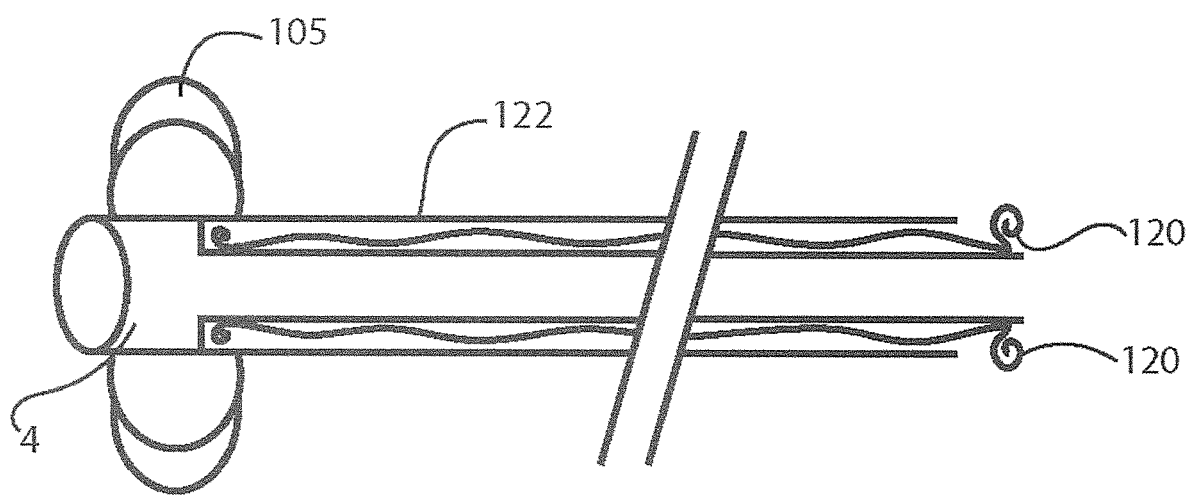
FIG. 23 is an illustration of an introducer sheath demonstrating a mechanism for deflection.

FIG. 23 shows one method by which the deflectability is achieved. In this case there are two wires 120 on opposite sides of the sheath that will attach to a handle that can be used to direct the distal tip 104 of the sheath to the area of interest. There is a balloon such as a PTFE balloon 105 at a distal end of the introducer sheath. At least portion of the distal end of the sheath may be of braided construction. At least portion of the sheath (such as the braided portion) may have a hydrophilic coating 122. FIG. 23 also illustrates control wires 120 extending from the distal end of the sheath to the proximal end to facilitate manipulation by the clinician.

Figure 24:
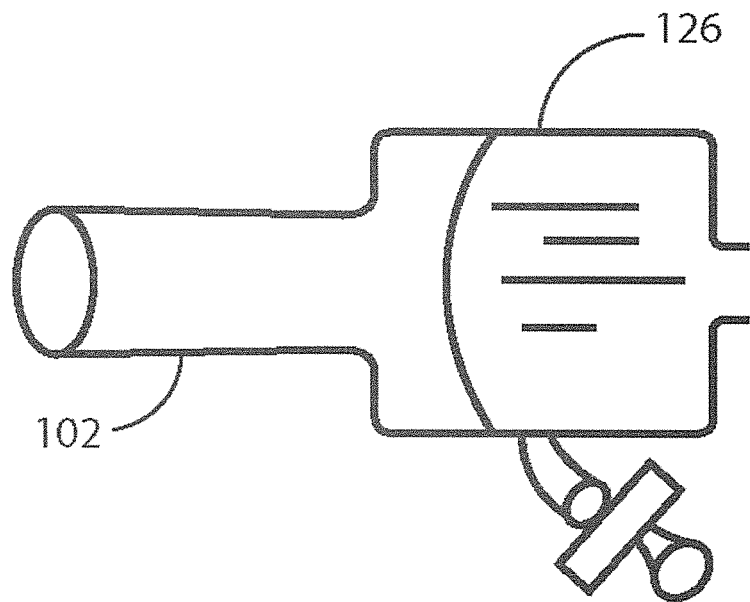
FIG. 24 is an illustration of the proximal end of the introducer sheath.

FIG. 24 shows the proximal end of an introducer sheath. This will consist of an ePTFE bladder seal that will provide adequate haemostasis. The seal will activate by insufflation of air of saline.

Figure 25:
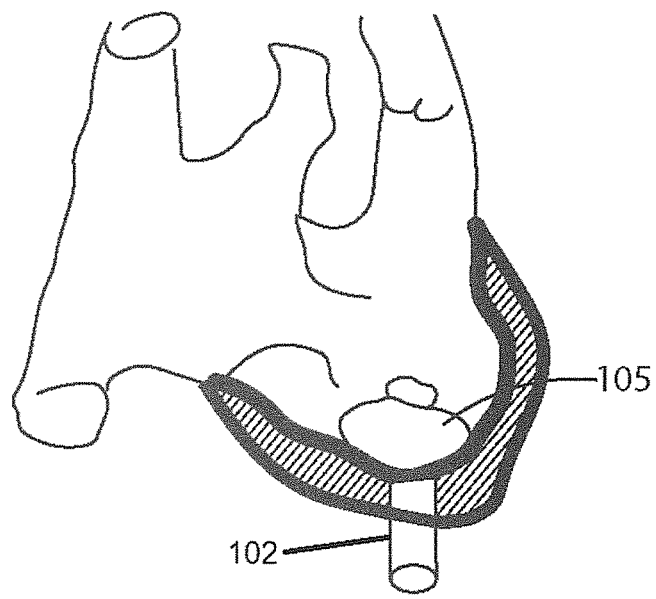
FIG. 25 shows the balloon acting as a retainer within a heart ventricle.

FIG. 25 illustrates a balloon 105 acting as a retainer and bumper. This feature will provide stability during the intervention ensuring sheath prolapse and subsequent bleeding do not occur.

The introducer sheath may be used as part of a system including a dilator as described. In some cases, the clinician may shape the shaft for a desired procedure. Alternatively or additionally, a separate steerable catheter may be delivered through the introducer sheath. One such steerable catheter is the SwiftNinja™ catheter from Merit Medical.

The introducer sheath may be used in a wide range of procedures, especially on the heart. The introducer sheath is particularly suitable for procedures requiring entry through a wall of the heart, especially in infants. For example, the introducer sheath may be used in procedures through the wall of the left ventricle or the considerably thinner wall of the right ventricle.

Example Method of Use

The surgeon gains access to the heart and then puts a purse-string on the wall 29 of the heart 30. The interventional cardiologist then punctures the heart wall 28 with a needle and passes a guidewire 27 through it. The hybrid sheath 2, with the dilator 20 inside, is passed over the guidewire into the heart 30. Using the markings on the sheath 2, the cardiologist can confirm that the distal end of the sheath is in the heart and remove the dilator 20. The balloon 5 can then be inflated through the side port 14 of the sheath. The sheath 2 can then be safely manipulated into position knowing that the balloon 5 is providing a safety bumper and the markings on the sheath indicate the depth of the sheath. The hybrid sheath can then be deflected, or steered, toward the area of the heart that device need to be directed at.

The importance of these features in small hearts is particularly important. The potential for inadvertent damage or bleeding can be particularly catastrophic in this patient cohort due to the smaller hearts and lower circulating blood volume.

Procedure

Use needle—Seldinger technique—to puncture a hole in the heart wall.

Insert guidewire 27.

Take out needle.

Introduce sheath 1 and dilator 20 over the guidewire 27.

Move up dilator tip 21 towards the heart wall 29.

Insert dilator tip 21 gently.

Push and twist—the dilator 20 makes a hole in the heart wall 29.

When the dilator 20 is in the heart, insert introducer sheath 1 over dilator 20.

Remove dilator 20.

Inflate balloon 5—acts primarily to stop the sheath from popping out through the hole in heart. Advance collar 6 along the sheath 1 until it is up against the heart wall 29. The catheter introducer sheath, by virtue of the inflated balloon 5 and the collar 6, is stabilised in position allowing further devices to be safely moved through the shaft of the introducer sheath.

Hybrid Procedures

The sheath of the invention is inserted directly through the right or left ventricles (or occasionally through the major arteries) to provide a more direct, safer route to the heart for performing complex interventions.

The heart is punctured under direct vision with a needle and a wire is advanced into the heart. The needle is removed and the sheath is advanced over the wire until it is in the desired location. The depth of the sheath within the heart may be confirmed by either one or both of external markers and radio-opaque markers.

When the sheath is in place, the distal balloon is inflated and the locking cuff is advanced towards the heart surface to optimise a stable sheath position.

Various catheters and devices can be advanced through the sheath to perform the intended intervention.

Percutaneous Procedures

In some cases the heart is accessed directly from the chest wall through the skin. An appropriate puncture site is identified and a needle is used to puncture the chest wall. The needle is advanced directly into the heart. When the needle is in place, a wire is advanced through the needle and the sheath of the invention is advanced into the heart in the same manner as described above.

The sheath of the invention may be used in a wide range of procedures. Some examples are as follows.

Example 1—Right Ventricular Outflow Tract (RVOT) Stenting

In infants with narrowing of the outflow tract to the lungs, pulmonary blood flow may be augmented by opening up the outflow tract using a stent.

The perventricular approach described above provides a more direct route to the heart, particularly in very small infants. The sheath of the invention is used to deliver a stent to the RVOT, facilitating stable sheath position for stent deployment.

Example 2—Branch Pulmonary Artery (PA) Stenting

A similar procedure to example 1 may be used for branch pulmonary artery stenting. In this case a stent is delivered slightly more distal in the lung arteries.

Example 3—Closure of a Ventricular Septal Defect (VSD)

A subxiphoid approach may be used for VSD closure in smaller infants.

In this procedure direct access is provided to the heart allowing delivery of larger VSD devices without concerns for hemodynamic instability caused by large delivery sheaths inserted from the groin.

The VSD is crossed and the sheath of the invention is used to advance and deploy a device across the septal defect (hole). The distal balloon avoids damage to the interior back wall of the heart by using the balloon as a "bumper" with a softer tip.

Example 4—Paravalvular Leak Closure

Direct access through the heart wall provides an optimal trajectory to the mitral valve. For patients who have required a mitral valve replacement and subsequently develop a leak around the surgically placed valve, it is necessary on occasion to seal this leak.

The sheath of the invention facilitates crossing the paravalvular leak from below with the balloon used to anchor the sheath on the atrial side of the leak. Inflation of the balloon may be used to simulate the position of the device ensuring that there is no potential impingement of the device on the mitral valve.

Example 5—Mitral Valve Intervention

A similar approach to Example 4 may be used for intervention on the mitral valve itself including balloon dilation of stent-valves in children placed surgically in the mitral position.

The invention is not limited to the embodiments hereinbefore described, which may be varied in construction and detail.

The invention claimed is:

1. An introducer sheath comprising:
a tubular shaft having a proximal end and a distal end; wherein the shaft comprises a distal tip that is more flexible than a main body of the shaft,
a balloon adjacent to the distal end of the shaft, said balloon having, on inflation, a toroidal shape; and
a proximal anchoring element having a release configuration in which the anchoring element is movable along the shaft and an anchoring configuration in which a tissue bridging gap, between the anchoring element located on a proximal side of the tissue bridging gap and the balloon located on a distal side of the tissue bridging gap, is reduced and the anchoring element is locked to the shaft,
wherein:
the anchoring element comprises a collar which is movable along the shaft,
the collar, in the release configuration is slidably movable along the shaft,
the collar has a distally facing end face that is configured for engaging one side of tissue of the tissue bridging gap, and said collar distal end face is only substantially flat; and
the anchoring element comprises a mounting system for mounting the collar to the shaft.

2. The introducer sheath as claimed in claim 1, wherein the balloon, on inflation, is configured to buffer the distal tip of the sheath away from tissue.

3. The introducer sheath as claimed in claim 1, wherein the balloon comprises a proximal portion and a distal portion, and wherein the proximal portion has a substantially flat proximal face.

4. The introducer sheath as claimed in claim 1, wherein at least the distal portion of the tubular shaft is malleable.

5. The introducer sheath as claimed in claim 1, wherein the mounting system comprises a housing, a shaft seal in the housing and first and second hub parts which retain the housing therebetween, the hub parts being adapted to lock the seal relative to the shaft; and wherein the collar is mounted to the housing.

6. The introducer sheath as claimed in claim 1, wherein the length of the tubular shaft is from 7 cm to 22 cm; and wherein the diameter of the tubular shaft is from 2 mm to 4.667 mm.

7. The introducer sheath as claimed in claim 1, wherein the shaft comprises a lumen through which fluid is delivered for inflation of the balloon; and wherein the distal tip of the shaft is deflectable; and wherein the distal tip of the sheath is movable in response to manipulation from a proximal end of the sheath; and further comprising control means extending from the distal end to the proximal end of the sheath.

8. The introducer sheath as claimed in claim 1, wherein the distal tip of the sheath is movable in response to manipulation from a proximal end of the sheath; and wherein at least a distal portion of the sheath is adapted for deflection in response to input from the proximal end of the sheath.

9. The introducer sheath as claimed in claim 1, wherein the shaft comprises marking to indicate the depth of insertion.

10. A hybrid method for accessing a heart comprising the steps of: providing an introducer sheath comprising a tubular shaft having a proximal end and a distal end; wherein the shaft comprises a distal tip that is more flexible than a main body of the shaft, a balloon adjacent to the distal end of the shaft; making an opening to provide an access point into the heart; with the balloon in a deflated configuration, inserting a distal portion of the introducer sheath through the incision; inflating the balloon to provide a safety bumper at the distal end of the sheath; and carrying out a procedure by passing devices through the sheath, wherein: the balloon at the distal end of the shaft having, on inflation, a toroidal shape; and a proximal anchoring element comprising a collar; the anchoring element having a release configuration in which the anchoring element is movable along the shaft and an anchoring configuration in which a tissue bridging gap, between the collar located on a proximal side of the tissue bridging gap and the balloon located on a distal side of the tissue bridging gap, is reduced and the anchoring element is locked to the shaft, wherein: the collar is movable along the shaft; the collar, in the release configuration is slidably movable along the shaft, and moves into the anchoring configuration in which the tissue bridging gap, between the collar located on the proximal side of the tissue bridging gap and the balloon located on the distal side of the tissue bridging gap, is reduced and the collar is locked to the shaft, wherein: the collar has a distally facing end face that is configured for engaging one side of tissue of the tissue bridging gap, and said collar distal end face is only substantially flat; and the anchoring element comprises a mounting system for mounting the collar to the shaft.

11. The method as claimed in claim 10, wherein making the opening comprises:
inserting a needle through the wall of the heart;
extending a dilator beyond the distal end of the introducer sheath to enlarge the opening made by the needle;
removing the needle;
inserting a guidewire through the opening; and
removing the dilator.

12. The method as claimed in claim 10, wherein the procedure comprises deploying a stent in the right ventricular outflow tract.

13. The method as claimed in claim 10, wherein the procedure comprises deploying a stent in a branch pulmonary artery.

14. The method as claimed in claim 10, wherein the procedures comprise closing a ventricular septal defect.

15. The method as claimed in claim 10, wherein the procedure comprises closure of a paravalvular leak.

16. The method as claimed in claim 10, wherein the procedure comprises manipulation of a heart valve.

17. A hybrid method for accessing a heart comprising the steps of: providing an introducer sheath comprising a tubular shaft having a proximal end and a distal end; wherein the shaft comprises a distal tip that is more flexible than a main body of the shaft, a balloon at the distal end of the shaft, and a proximal anchoring element comprising a collar proximal of the balloon; making an opening to provide an access point into the heart; with the balloon in a deflated configuration, inserting a distal portion of the introducer sheath through the incision; inflating the balloon; advancing the collar towards the balloon; locking the collar in a desired position on the shaft; and carrying out a procedure by passing devices through the sheath, wherein: the balloon at the distal end of the shaft having, on inflation, a toroidal shape; and the anchoring element having a release configuration in which the anchoring element is movable along the shaft and an anchoring configuration in which a tissue bridging gap, between the collar located on a proximal side of the tissue bridging gap and the balloon located on a distal side of the tissue bridging gap, is reduced and the anchoring element is locked to the shaft, wherein: the collar is movable along the shaft, the collar, in the release configuration is slidably movable along the shaft, and moves into an anchoring configuration in which the tissue bridging gap, between the collar located on the proximal side of the tissue bridging gap and the balloon located on the distal side of the tissue bridging gap, is reduced and the collar is locked to the shaft, wherein: the collar has a distally facing end face that is configured for engaging one side of tissue of the tissue bridging gap, and said collar distal end face is only substantially flat; and the anchoring element comprises a mounting system for mounting the collar to the shaft.

* * * * *